United States Patent [19]

Bocchi et al.

[11] Patent Number: 5,033,467
[45] Date of Patent: Jul. 23, 1991

[54] COMBINED DEFIBRILLATOR PACER SYSTEM UTILIZING PACER TIP LEAD SWITCH

[75] Inventors: David E. Bocchi, Vadnais Heights; Stanley M. Bach, Jr., Shoreview, both of Minn.

[73] Assignee: Cardiac Pacemakers, Inc., St. Paul, Minn.

[21] Appl. No.: 600,266

[22] Filed: Oct. 23, 1990

Related U.S. Application Data

[63] Continuation of Ser. No. 394,663, Aug. 16, 1989, abandoned.

[51] Int. Cl.$^5$ .............................................. A61N 1/362
[52] U.S. Cl. .......................... 128/419 D; 128/419 PG
[58] Field of Search .................... 128/419 PG, 419 D

[56] References Cited

U.S. PATENT DOCUMENTS 4,787,389 11/1988 Tarjan ............................ 128/419 D
4,827,936 5/1989 Pless et al. ..................... 128/419 D Primary Examiner—William E. Kamm
Assistant Examiner—Scott M. Getzow
Attorney, Agent, or Firm—Fleit, Jacobson, Cohn, Price, Holman & Stern

[57] ABSTRACT

A switch for placement in the lead line connecting a pacing pulse generator to an implanted pacing tip electrode in a combined implantable pacing-defibrillation system. The switch is triggered by switch control circuitry to open during defibrillation and to close during pacing. When the switch is open, the implantable unit is electrically isolated from the high voltage defibrillation pulse delivered to the heart. When the switch is closed, a low resistance conduction path is provided in the pacing lead to the pacing tip electrode.

13 Claims, 2 Drawing Sheets

COMBINED DEFIBRILLATOR PACER SYSTEM UTILIZING PACER TIP LEAD SWITCH

This application is a continuation of application Ser. No. 07/394,663, filed Aug. 16, 1989, now abandoned.

BACKGROUND OF THE INVENTION

The present invention relates to a combined implantable defibrillator-pacer cardiac treatment system utilizing a pacer tip lead switch for the protection of the electronics during high-energy defibrillation.

One arrangement of a combined implantable defibrillator-pacer includes a bipolar pacing tip mounted on the heart and two patch electrodes mounted on or about the heart for defibrillating the heart. The two patch electrodes may be designated a defibrillation patch and a common patch. In such an arrangement the pace output conduction path is from the bipolar pacing tip to the common patch electrode. The defibrillation conduction path is from the defibrillation patch electrode to the common patch electrode. One problem encountered by this configuration is that during high voltage defibrillation, the pacing tip electrode acts as a probe and conveys the high voltage delivered during defibrillation to the input of the implantable device. This high voltage would normally destroy the implantable device. One way to prevent this from occurring is to place a diode, with its anode connected to the pacing tip and its cathode connected to common, between the pacing tip electrode and the common return path. This diode clamps the high potential seen at the pacing tip and protects the device from the high voltage during defibrillation. However, this diode creates a further problem.

By placing the diode between the pacing tip and the common return path, a current conduction path is treated from the high voltage defibrillation patch electrode, through the heart, through the pacing tip electrode, and through the diode to the common return path. This current can be as high as 4 amps, which is sufficient to burn myocardial tissue at the pacing tip-electrode interface, as well as increase pacing thresholds.

One solution is to open this current conduction path by placing a large resistance in series with the pacing tip lead to limit the current therethrough. However, since the implantable unit is also used as pacemaker, such a large resistance attenuates the pacing pulse amplitude to such a low level that pacing the heart becomes practically impossible without dramatically increasing input energy requirements.

SUMMARY OF THE INVENTION

It is a primary object of the present invention to overcome the above-stated problems and provide an implantable combined defibrillator-pacer capable of efficiently delivering both a defibrillation pulse and pacing pulses without the danger of destroying the implantable device or damaging myocardial tissue caused by a current conduction path from a pacing tip through the heart to the common return path during defibrillation.

It is an additional object of the present invention to provide a switch in the pacing tip lead which allows an implantable combined defibrillator-pacer unit to pace into a low impedance, but also prevent any current from flowing through the pacing tip lead during an internally delivered defibrillation pulse.

It is yet a further object of the present invention to provide a switch in the pacing tip lead which limits the current flowing through the pacing tip lead during an externally delivered defibrillation pulse.

The above and other objects and advantages of the present invention will become more apparent when reference is made to the following description, taken in conjunction with the accompanying drawings.

DETAILED DESCRIPTION OF THE DRAWINGS

Figure 1:
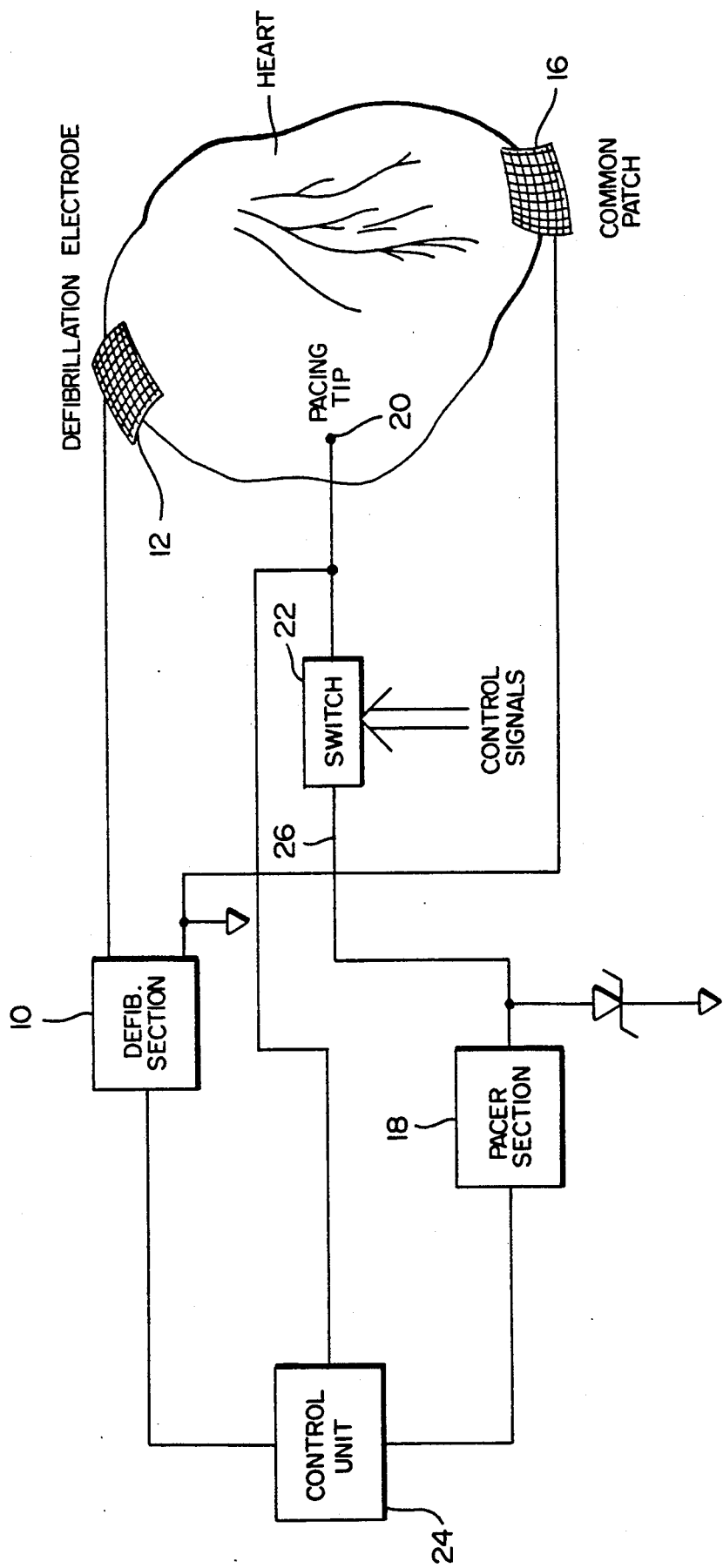
FIG. 1 is a schematic representation of a combined implantable defibrillator-pacer system including a controllable switch in the pacing lead in accordance with the present invention.

Referring first to FIG. 1, a combined defibrillator-pacer system is illustrated and comprises a defibrillation section 10 which connects to a defibrillation electrode 12 mounted on or about the heart, and to a common patch electrode 16 mounted on or about the heart. In addition, a pacer section 18 is provided and connects to a pacing tip electrode 20 mounted on or about the heart, via a controllable switch 22. The switch 22 is controlled by a plurality of control signals, to be described in more detail hereinafter.

The defibrillation section 10 and the pacer section 18 are controlled by a control unit 24. The control unit 24 may comprise an ECG amplifier and other ECG analyzing devices for determining the type of treatment to be applied to the heart. The pacing tip 2 is typically capable of sensing the cardiac activity of the heart and providing such sensed information to the control unit 24.

The pacer section 18 connects to the pacing tip 20 via lead line 26. The switch 22 is typically mounted in the lead line 26 between the pacer section 18 and the pacing tip 20.

The switch 22 is controlled by the control signals to open or close, thus selectively providing a current path from the pacing tip 20 to the pacer section 18.

Figure 2:
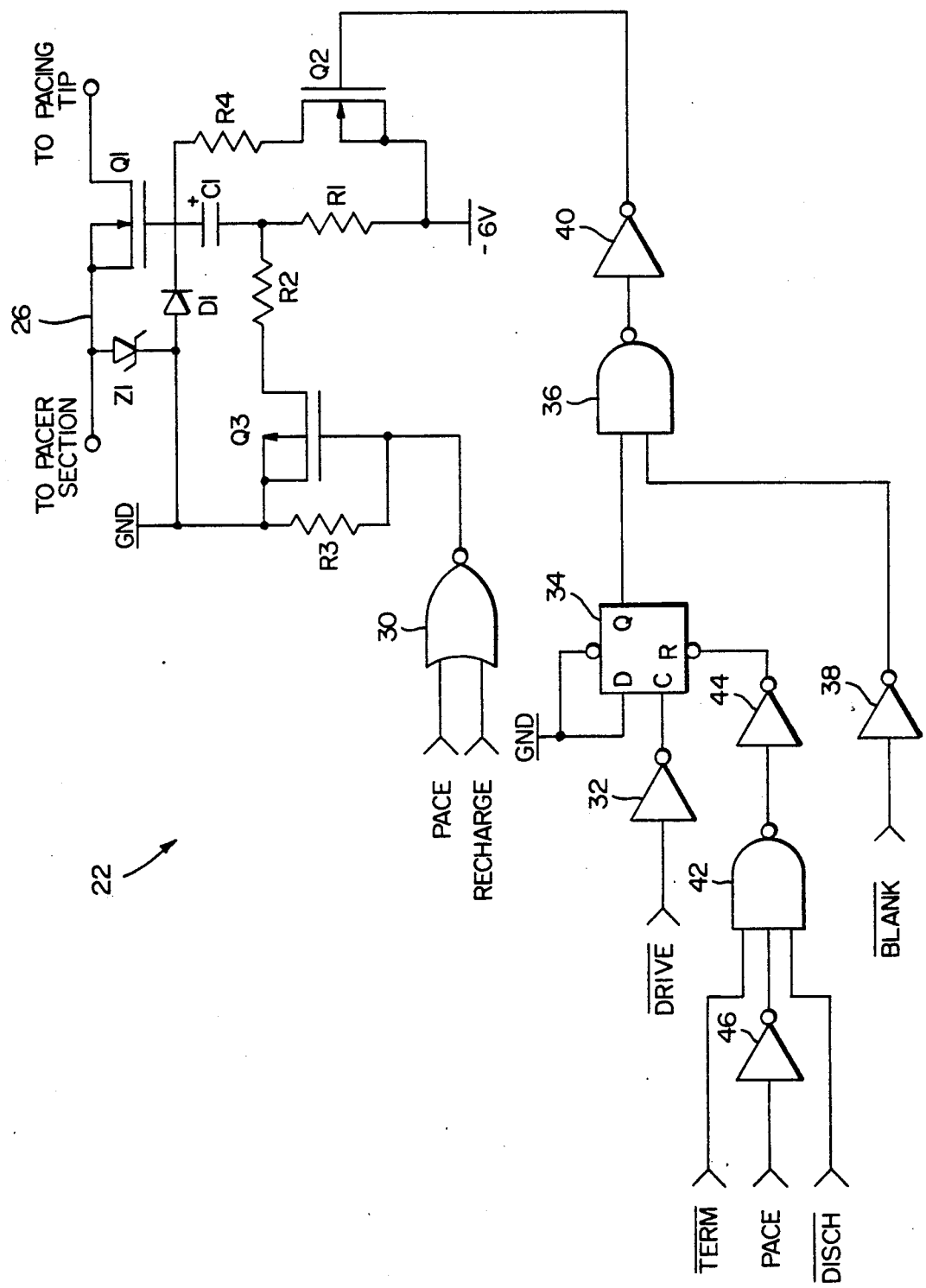
FIG. 2 is a schematic diagram illustrating the switch in the pacing tip lead of the present invention.

FIG. 2 illustrates an electrical schematic diagram whereby specific control signals are used to control the switch 22. These control signals include PACE, RECHARGE, TERM, DISCHARGE, DRIVE, and BLANK. As mentioned above, the switch 22 should be open when a defibrillation pulse is being delivered to the heart so that the high energy defibrillation pulse is not picked up by the pacing tip 20 and conveyed to the pacer section 18. On the other hand, the switch 22 should close when a pacing pulse is delivered to the heart via the pacing tip 20. In FIG. 2, the transistor Q1, shown as a MOSFET transistor is connected in the lead line 26 between the pacing tip 20 and the pacer section 18. Transistor Q1 is selectively turned on and off to close and open, respectively, the lead line 26.

The signals PACE and RECHARGE trigger the transistor Q1 to turn on and thus provide a conduction path between the pacer section 18 and the pacing tip 20. The transistor Q1 is normally off, and thus the lead line 26 is normally open. The capacitor C1 which is connected to the gate of transistor Q1 is charged to 6 volts through the diode D1 and resistor R1. The resistor R1 is connected to a negative 6 volt power supply. To turn on the transistor Q1, when the PACE or RECHARGE signals are high, the P-channel MOSFET transistor Q3 is triggered by the NOR gate 30 to boost the capacitor C1 6 volts above ground. This forces a positive 6 volts onto the gate of the transistor Q1. During pacing, the source of the transistor Q1 is negative with respect to ground. During recharging, on the other hand, the source of the transistor Q1 is less than 3 volts above ground. As such, when the gate of the transistor Q1 is held at positive 6 volts by the capacitor C1, the gate to source voltage of the transistor Q1 is above its threshold, thus turning the transistor Q1 on. With the transistor Q1 on, pacing or recharging current is permitted to flow through the lead line 26 to the tip lead 20.

During defibrillation, the transistor Q1 is held in its off state to prevent current from flowing in the lead line 26. The signals DRIVE and BLANK are high during the capacitor charge mode and defibrillation. These signals turn on the MOSFET transistor Q2 after passing through several digital logic gates. Specifically, the DRIVE signal is connected via an inverter 32 to the clock input of a D-type flip-flop 34. The output of the flip-flop 34 is fed to a NAND gate 36. The signal BLANK is also fed to the NAND gate 36 via an inverter 38. The output of the NAND gate 36 is fed to the gate of the transistor Q2 via an inverter 40. When the signals DRIVE and BLANK are detected, the transistor Q2 is turned on, thereby keeping the gate of the transistor Q1 one diode drop below ground. When the tip potential increases with respect to common during defibrillation, the source and drain of the transistor Q1 will go positive. The source will try to follow the drain, but when the source exceeds the diode drop of the zener diode Z1, the source will be clamped to one diode drop above ground. Because the gate of the transistor Q1 is clamped to one diode drop below ground, there is not enough gate to source voltage to turn the transistor Q1 on. Therefore, the transistor stays off and no current flows through the lead line 26. The transistor Q1 is designed to typically withstand at least 800 volts before breaking down.

To reset the transistor Q1 back to its normally off state, the signals TERM and DISCHARGE are detected through the NAND gate 42 which is connected to the reset input of the flip-flop 34 via an inverter 44. The PACE signal is also connected to an input of the NAND gate 42 via an inverter 46. When the appropriate combination of the signals TERM, PACE, and DISCHARGE are detected, the transistor will be reset to its normally off state.

If an external defibrillation pulse is applied to the patient, the source of the transistor Q1 is held one diode drop above ground so that the transistor Q1 turns off automatically for the same reasons stated above. That is during external defibrillation, the gate of transistor Q1 is one diode drop below ground. When the tip potential rises with respect to common during external defibrillation, the source follows the drain. Zener diode Z1 holds the source of transistor Q1 one diode drop above ground thereby preventing transistor Q1 from turning on. Under these conditions, gate potential is below threshold and hence transistor Q1 is off and no current flows through the pacing tip.

The above description is intended by way of example only and is not intended to limit the present invention in any way except as set forth in the following claims.

We claim:

1. A system for performing both cardiac pacing and defibrillation, said system comprising:

defibrillation means for generating a defibrillation pulse;

defibrillation electrode means connected to said defibrillation means for delivering said defibrillation pulse to the heart of a patient;

pacing means for generating pacing pulses;

pacing electrode means for delivering said pacing pulses to the heart of said patient;

control means responsive to sensed cardiac activity for generating switch control signals and triggering either said defibrillation means to generate said defibrillation pulse or said pacing means to generate said pacing pulses;

switch means connected between said pacing electrode means and said pacing means and capable of assuming first and second states; and switch control means directly receiving and responsive to said switch control signals for triggering said switch means to assume said first state whereby a conduction path is provided between said pacing means and said pacing electrode means for delivering said pacing pulses to the heart, and for triggering said switch means to assume said second state whereby no conduction path is provided between said pacing means and said pacing electrode means.

2. The system of claim 1, wherein said switch control means is responsive to a first set of said switch control signals to place said switch means in said first state, and is responsive to a second set of said switch control signals to place said switch means in said second state.

3. The system of claim 1, wherein said switch means is a MOSFET transistor.

4. In a combined implantable cardiac pacer-defibrillator system including a pacing pulse generator connected via a pacer lead line to an implanted pacing tip electrode, a defibrillation pulse generator connected to implanted defibrillation electrodes for delivering a high voltage defibrillation pulse via said defibrillation electrodes to the heart, and a control means responsive to sensed cardiac activity, coupled between said pacing pulse generator and defibrillation pulse generator, for generating switch control signals, the improvement comprising a switch means connected in said pacer lead line between said pacing pulse generator and said pacing tip electrode, and switch control means directly receiving and responsive to said switch control signals from said control means for selectively opening an closing said switch means to selectively isolate said pacing pulse generator from said high voltage defibrillation pulse.

5. The system of claim 5, wherein said switch means is a MOSFET transistor switch for placement in a pacer lead line between the pacing pulse generator and the pacing tip of the combined implantable cardiac pacer-defibrillator unit, said MOSFET transistor switch comprising a source, gate, and drain, said source being connected in said pacer lead line proximate said pacing pulse generator and said drain being connected in said pacer lead line proximate said pacing tip, said gate being operatively connected to said switch control means so that said switch is triggered by said switch control means, based upon control signals received from said control means, to, on the one hand, open during defibrillation so as to isolate said implantable unit from a high voltage defibrillation pulse delivered to the heart, and on the other hand, to close so as to provide a low impedance conduction path from the pacing pulse generator to said pacing tip for pacing the heart.

6. The system of claim 4, wherein said switch means is a MOSFET transistor.

7. A system for performing both cardiac pacing and defibrillation; the system comprising:
a defibrillation pulse generator for generating a defibrillation waveform;
a pacing pulse generator for generating pacing pulses;
ECG analyzing means for analyzing the ECG of the heart and triggering said pacing pulse generator to issue pacing pulses or triggering said defibrillation pulse generator to issue said defibrillation waveform;
first and second defibrillation electrodes adapted to be mounted on or about the heart and connected to said defibrillation pulse generator for delivering said defibrillation waveform to the heart;
a pacing electrode adapted to be mounted on or about the heart and connected to said pacing pulse generator for delivering said pacing pulses to the heart;
a pacing lead line connecting said pacing pulse generator to said pacing electrode;
a MOSFET transistor switch connected in said pacing lead line for selectively opening and closing said lead line;
switch control circuitry directly receiving and responsive to switch control signals from said ECG analyzing means for triggering said transistor switch to close during pacing to provide a conduction path in said pacing lead line from said pacing pulse generator to said pacing electrode, and triggering said transistor switch to open during defibrillation to electrically isolate said pacing pulse generator, defibrillation pulse generator and said eCG analyzing means from the heart.

8. An implantable system for performing both cardiac pacing and defibrillation of a heart, said system comprising:
defibrillation means for generating defibrillation pulses;
pacing means for generating pacing pulses;
control means for analyzing heart activity, generating a first control signal upon determining that pacing of the heart is necessary based on the heart activity, generating a second control signal upon determining that defibrillation of the heart is necessary based on heart activity and triggering said pacing means to issue said pacing pulses in response to the first control signal or said defibrillation means to issue said defibrillation pulses in response to the second control signal;
pacing electrode means for delivering said pacing pulses from said pacing means to the heart;
defibrillation electrode means for delivering said defibrillation pulses from said defibrillation means to the heart;
switch means connected between said pacing electrode means and said pacing means and capable of connecting and disconnecting said pacing electrode means from said pacing means; and
switch control means, responsive to the first and second control signals from the control means, for triggering said switch means to connect said pacing electrode means to said pacing means when pacing the heart and triggering said switch means to disconnect said pacing electrode means from said pacing means when defibrillating the heart.

9. An implantable system for performing both cardiac pacing and defibrillation of a heart, comprising:
control means for analyzing heart activity and generating first and second control signals used to treat the heart based upon analysis of the heart activity;
first means for generating high energy pulses in response to said first control signal from said control means;
second means for generating pulses of substantially less energy than the high energy pulses in response to said second control signal from said control means;
first electrode means connected to said first generating means for delivering said high energy pulses generated by said first generating means to the heart;
second electrode means for delivering said pulses of substantially less energy generated by said second generating means to the heart;
switch means connected between said first generating means and said first electrode means; and
switch control means responsive to the first and second control signals for triggering said switch means to an open position to disconnect said first generating means from said first electrode means and triggering said switch means to a closed position to connect said first generating means to said first electrode means to prevent said second means from receiving the high energy pulses during defibrillation.

10. A system as claimed in claim 9, wherein said first generating means generates defibrillation pulses as said high energy pulses in response to said first control signal from said control means.

11. A system as claimed in claim 9, wherein said second generating means generates pacing pulses as said substantially less energy pulses in response to said second control signal from said control means.

12. An implantable system for performing both cardiac pacing and defibrillation of a heart, said system comprising:
defibrillation means for generating defibrillation pulses;
pacing means for generating pacing pulses;
control means for analyzing heart activity, generating a first control signal upon determining that pacing of the heart is necessary based on the heart activity, generating a second control signal upon determining that defibrillation of the heart is necessary based on heart activity and triggering said pacing means to issue said pacing pulses in response to the first control signal or said defibrillation means to issue said defibrillation pulses in response to the second control signal;
pacing electrode means for delivering said pacing pulses from said pacing means to the heart;
defibrillation electrode means for delivering said defibrillation pulses from said defibrillation means to the heart;
a pacer lead line connected between said pacing means and said pacing electrode means;
switch control means responsive to the first and second control signals generated by said control means;
a MOSFET transistor switch for placement in said pacer lead line between said pacing means and said pacing electrode means, wherein said MOSFET transistor switch comprises a source, gate, and drain, said source being connected in said pacer lead line proximate said pacing means, said drain being connected in said pacer lead line proximate said pacing electrode means and said gate being operatively connected to said switch control means so that said switch is triggered by said switch control means to open during defibrillation so as to isolate said implantable unit from a high voltage defibrillation pulse delivered to the heart or to close so as to provide a low impedance conduction path from the pacing means to said pacing electrode means for pacing the heart.

13. In a combined implantable cardiac pacer-defibrillator system including a pacing pulse generator, a pacing tip electrode, and a pacer lead line connecting the pacing tip electrode to the pacing pulse generator for delivering pacing pulses via said pacing tip electrode to the heart, a defibrillation pulse generator implanted defibrillation electrodes connected to the defibrillation pulse generator for delivering a defibrillation shock to the heart, and a control means coupled between said pacing pulse generator and defibrillation pulse generator for analyzing heart activity and for generating a first control signal upon determining that pacing of the heart is necessary based on the heart activity, generating a second control signal upon determining that defibrillation of the heart is necessary based on heart activity and triggering said pacing means to issue said pacing pulses in response to the first control signal or said defibrillation means to issue said defibrillation pulses in response to the second control signal, the improvement comprising:

switch means connected in said pacer lead line between said pacing electrode means and said pacing means and capable of connecting and disconnecting said pacing electrode means from said pacing means; and switch control means responsive to the first and second control signals generated by the control means for triggering said switch means to connect said pacing pulse generator to said pacing tip electrode and triggering said switch means to disconnect said pacing electrode means from said pacing means to prevent the defibrillation shock from being picked up by the pacing tip electrode and communicated to the pacing pulse generator.

* * * * *